United States Patent
Brown et al.

(10) Patent No.: US 8,986,392 B2
(45) Date of Patent: Mar. 24, 2015

(54) FEMORAL IMPLANT

(76) Inventors: S. Gary Brown, Alamo, CA (US);
Gregory Thomas Van Der Meulen, Ketchum, ID (US); Christopher G. Sidebotham, Mendham, NJ (US)

( * ) Notice: Subject to any disclaimer, the term of this patent is extended or adjusted under 35 U.S.C. 154(b) by 287 days.

(21) Appl. No.: 13/218,282

(22) Filed: Aug. 25, 2011

(65) Prior Publication Data
US 2013/0053977 A1    Feb. 28, 2013

(51) Int. Cl.
*A61F 2/36* (2006.01)
*A61B 17/16* (2006.01)
*A61F 2/30* (2006.01)
*A61B 17/74* (2006.01)

(52) U.S. Cl.
CPC ... *A61B 17/1668* (2013.01); *A61F 2002/30574* (2013.01); *A61F 2002/3631* (2013.01); *A61F 2/3601* (2013.01); *A61F 2/3676* (2013.01); *A61F 2002/30242* (2013.01); *A61F 2002/30807* (2013.01); *A61F 2002/30884* (2013.01); *A61F 2002/3092* (2013.01); *A61F 2002/30932* (2013.01); *A61F 2002/30985* (2013.01); *A61F 2310/00796* (2013.01); *A61B 17/742* (2013.01)

USPC .............. 623/23.14; 623/23.21; 623/23.3

(58) Field of Classification Search
USPC .......... 623/19.11–1.914, 21.11–21.17, 21.19, 623/22.41–22.46, 23.15–23.35, 623/23.12–23.14, 23.42
See application file for complete search history.

(56) References Cited

U.S. PATENT DOCUMENTS

| | | | | |
|---|---|---|---|---|
| 4,944,762 | A * | 7/1990 | Link et al. .................. | 623/23.21 |
| 6,312,473 | B1 * | 11/2001 | Oshida ........................ | 623/23.55 |
| 7,854,768 | B2 * | 12/2010 | Wiley et al. ................ | 623/19.14 |
| 2006/0009852 | A1 * | 1/2006 | Winslow et al. ............ | 623/19.14 |
| 2010/0023131 | A1 * | 1/2010 | Crofford et al. ............ | 623/23.11 |
| 2010/0324691 | A1 * | 12/2010 | Brunnarius ................ | 623/19.11 |

* cited by examiner

*Primary Examiner* — Thomas J Sweet
*Assistant Examiner* — Megan Wolf
(74) *Attorney, Agent, or Firm* — Klarquist Sparkman, LLP

(57) ABSTRACT

A femoral implant includes a main shaft with a proximal end and a smooth distal end. A porous circumferential collar is provided between the proximal end and distal end, and a porous distally-extending portion extends distally from the collar to provide for additional bone ingrowth.

6 Claims, 8 Drawing Sheets

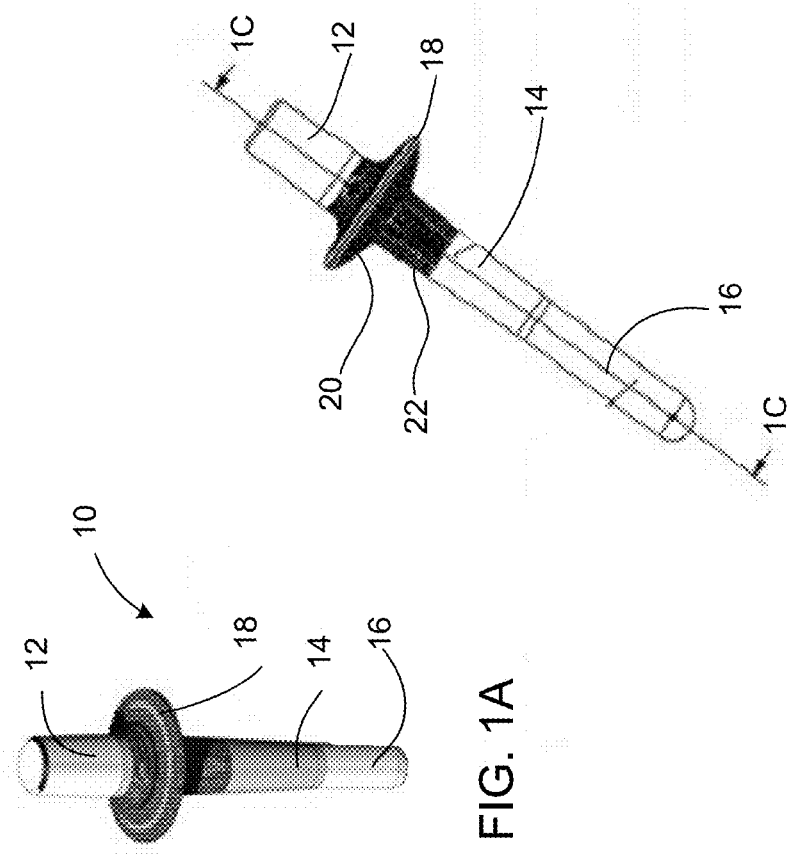
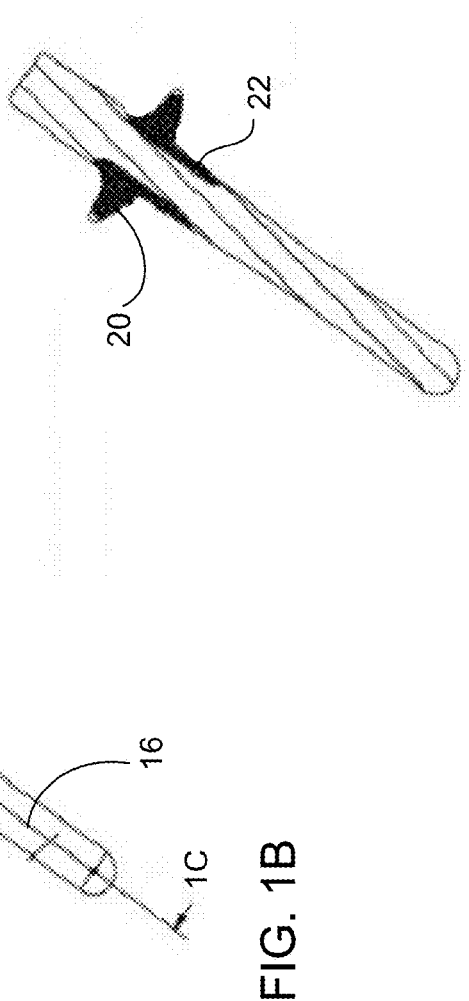
FIG. 1A
FIG. 1B
FIG. 1C

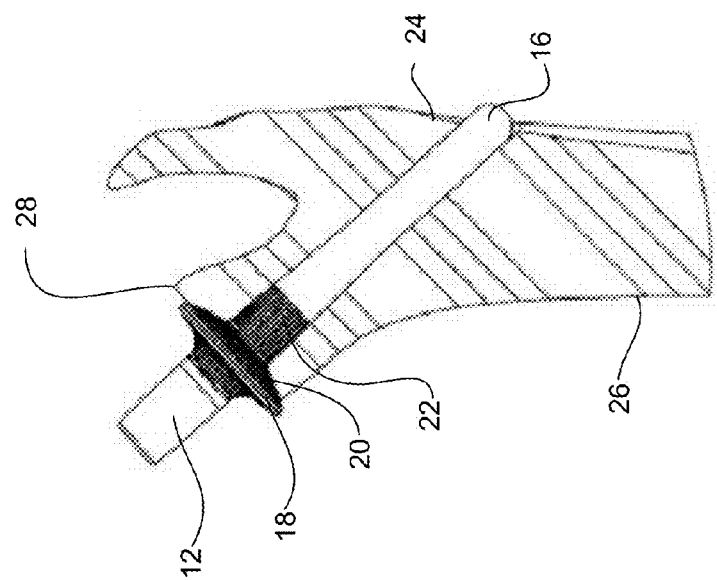
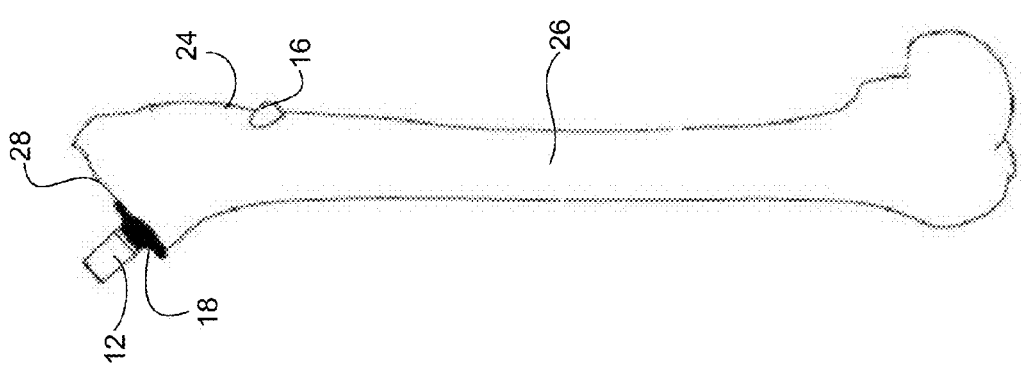

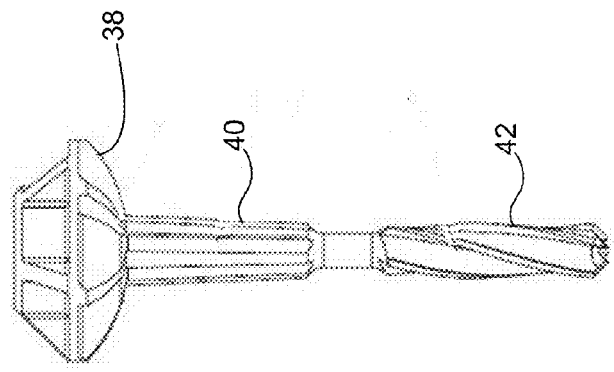
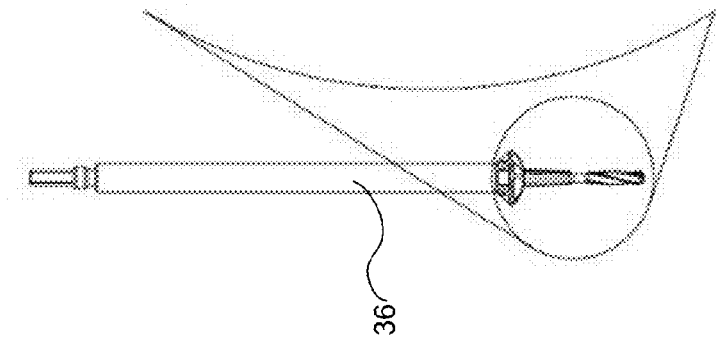
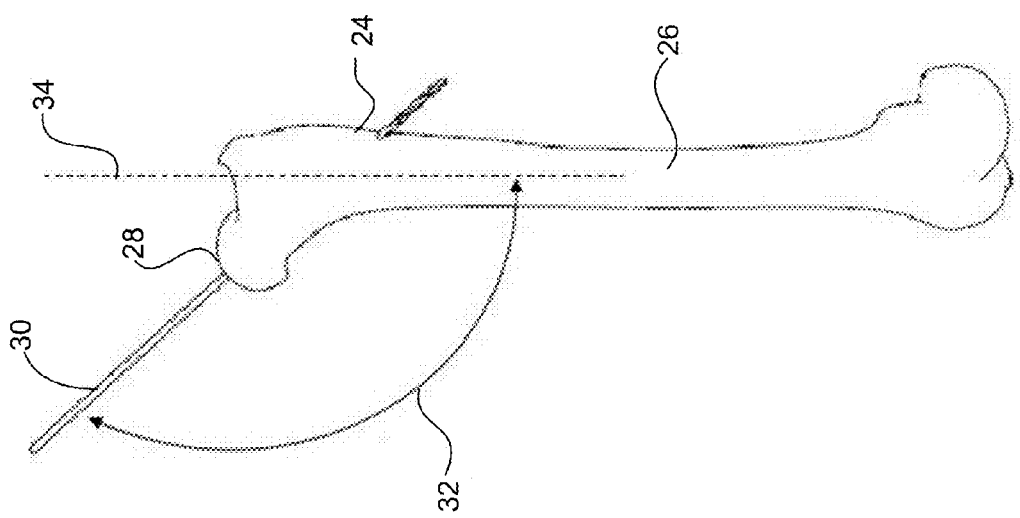

FEMORAL IMPLANT

FIELD

The present disclosure concerns embodiments of a femoral hip implant and methods for implanting femoral hip implants.

BACKGROUND

In total hip replacement, there are several designs which address different indications for hip replacement depending on the quality and geometry of the patient's bones. Hip implants generally replace the femoral head and the acetabular socket with the objectives of restoring stable pain-free motion. There are several different designs of femoral components. In some designs, just the surface of the femoral head is replaced, while other designs are composed of a stem and head-neck section.

With resurfacing designed femoral components, minimal bone is removed; however complications with implant loosening can occur due to the ability of the bone to support the implant. With the stemmed femoral components, the implant is fixed within the canal of the femur. The effectiveness of this design is dependent, at least in part, on the strength of the cancellous bone within the canal of the femur. Without proper strength, the stem can subside (sink) further into the canal creating instability and, in some cases, fractures. Both scenarios can result in undesirable revision surgery.

SUMMARY

In one embodiment, a bone implant apparatus is provided. The apparatus includes a proximal end portion, a central tapered body with a distal end portion, and a circumferential collar positioned between the proximal end portion and the distal end portion of the central tapered body. The circumferential collar comprises a porous material capable of allowing bone ingrowth into the collar. A distally-extending portion extending from the collar toward the distal end portion can also be formed of a porous material capable of allowing bone ingrowth into the distally-extending portion. The central tapered body can tapers from the distally-extending portion to the distal end portion.

In some implementations, the proximal end portion can be integral with the distal end portion forming a main shaft, and the collar is secured to the main shaft between the proximal and distal end portions. The distally-extending portion can be a porous body disposed circumferentially around the main shaft distal to the circumferential collar. The circumferential collar further can include a substantially spherical distal surface. The distal end portion of the apparatus can be substantially smooth and formed of a material that restricts bone ingrowth. In some implementations, the proximal end portion can be tapered, with the proximal end portion being at its widest in the vicinity of the collar and at its narrowest furthest from the collar.

In some embodiments, the bone implant apparatus is configured to be implanted without using any cement or other bonding agents to bond the implant to the bone of the femur. The bone implant apparatus can also be sized to be sufficiently long so that at least a portion of the distal end portion extends through a lateral cortex of a femur of a subject when implanted therein.

In another embodiment, a method for total hip replacement is provided. The method can include inserting a pin into a neck of a femur and through a lateral cortex of the femur to create an opening in the femur and provide a guide for a cannulated cutter, forming an enlarged opening in the femur by passing the cannulated cutter over the pin, and inserting an implant into the enlarged opening created by the cannulated cutter. The cannulated cutter can include a distal cylindrical cutting portion, a tapered central cutting portion, and a proximal spherical cutting portion.

During implantation, the pin can be oriented at substantially the same angle as the true neck of the femur. The implant can have a proximal end portion, a distal end portion, and a circumferential collar positioned therebetween. The circumferential collar can have a substantially spherical distal surface and as the cannulated cutter passes over the pin to enlarge the opening in the femur, the proximal spherical cutting portion can form a surface in the femur that is sized to receive the spherical distal surface of the collar. The circumferential collar can comprise a porous material capable of allowing bone ingrowth into the collar when the implant is received in the enlarged opening.

In some implementations, the inserting of the implant into the enlarged opening can include press-fitting the implant into the enlarged opening. The implant can compress the cancellous bone to provide fixation. In other implementations, the forming of the enlarged opening can include passing the distal cylindrical cutting portion through a lateral cortex of the femur, and the inserting of the implant into the enlarged opening can include causing a distal end portion of the implant to extend out of the lateral cortex of the femur. The distal end portion of the implant can at least partially contact the cortical bone of the lateral cortex to help provide stability of the implant. In some implementations, both ends of the implant can be supported by cortical bone, with a distal end of the implant contacting cortical bone in the vicinity of the lateral cortex and a proximal end of the implant contacting cortical bone in the neck of the femur.

The foregoing and other objects, features, and advantages of the invention will become more apparent from the following detailed description, which proceeds with reference to the accompanying figures.

BRIEF DESCRIPTION OF THE DRAWINGS

FIG. 1A is an isometric view of a femoral hip implant.

FIG. 1B is a side elevation view of a femoral hip implant.

FIG. 1C is a cross-sectional view of a femoral hip implant, taken along line 1C-1C in FIG. 1B.

FIG. 2 is a side elevation view of a femoral implant in place in a femur.

FIG. 3 is a partial cross-sectional view of a femoral implant in place in a femur.

FIG. 4 is a side elevation view showing insertion of a pin into a femur in preparation for placing a femoral implant.

FIG. 5A is a side elevation view of a cannulated compound cutter.

FIG. 5B is an enlarged view of the cannulated compound cutter shown in FIG. 4, showing three separate cutting geometries.

DETAILED DESCRIPTION

Figure 6C:
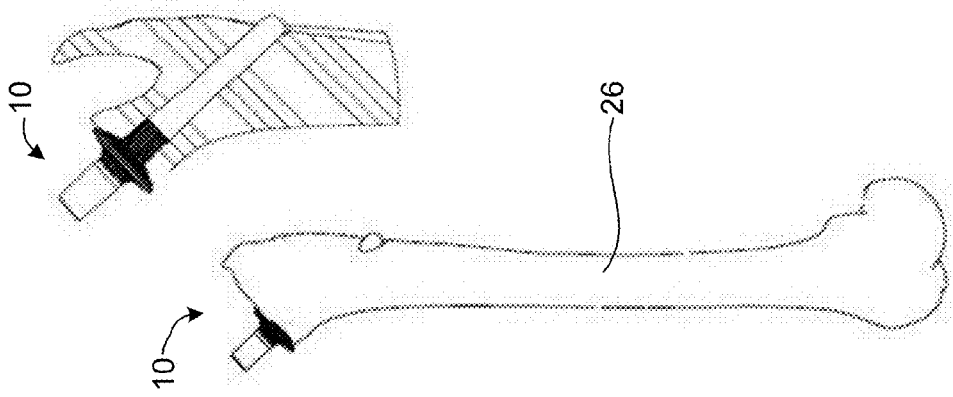
FIG. 6C is a side elevation view showing a femoral implant installed in a femur.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

As used herein, the term "porous" means a structure having one or more openings, gaps, or other such surfaces that allow bone to grow into the structure and mechanically interlock with the structure. "Bone ingrowth" refers to the growing of bone into a porous structure in a manner that allows the bone to interlock with the structure. "Bone ongrowth" refers to the growing of bone on a surface of a structure in a manner so that the bone growth contacts the structure without generally interlocking with that structure.

The femoral hip implants and methods of use disclosed herein provide improved femoral implant fixation. In particular, instead of relying solely on softer cancellous bone, the femoral hip implants disclosed herein can interact with harder cortical bone to provide improved stability. In addition, at least in some embodiments, the disclosed femoral hip implants provide a bone conserving approach, reducing the amount of bone that is removed and the occurrence of complications common with conventional hip implants.

FIGS. 1A-1C depict an embodiment of a femoral hip implant 10. Femoral hip implant 10 comprises a proximal end 12, a centrally tapered body 14 with a distal end 16, and a circumferential collar 18 positioned between proximal end 12 and centrally tapered body 14. Proximal end 12, centrally tapered body 14, and collar 18 can be integrally formed as a single structure.

Collar 18 can comprise a substantially spherical distal surface 20. The spherical surface of the collar can provide improved stress distribution. With a flat collar, when the implant is loaded, the contact quickly becomes highly focused around a small point leading to high stresses. The spherical collar provides for better stress distribution through a larger area contact at loading.

Collar 18 can comprise a generally porous material to allow for bone ingrowth into collar 18. As shown in FIGS. 1A-1C, collar 18 can have a distally-extending portion 22 of porous material. Distally-extending portion 22 preferably tapers in the same manner as tapered body 14, forming one generally contiguous tapered shape. As noted above, implant 10 can be formed as a single integral structure. However, if desired, portions of the implant can be formed separate from the main body of the implant and coupled together. For example, distally-extending portion 22 can be formed as part of a collar that can be separately attached to the implant.

FIGS. 2 and 3 illustrate femoral hip implant 10 fixed within a femur of a subject. As shown in FIGS. 2 and 3, when implanted into a subject, distal end 16 of femoral hip implant 10 extends out the lateral cortex 24 of the femur 26, while proximal end 12 of femoral hip implant 10 extends out of the neck 28 of the femur 26. Thus, collar 18 provides proximal support for the implant utilizing the cortical bone of the femoral neck 28, and spherical distal surface 20 of the circumferential collar 18 provides for stress distribution across a large area, reducing the formation of stress concentrations in bone that is in the vicinity of collar 18. Since both ends (i.e., distal end 16 and proximal end 12) of the femoral hip implant utilize cortical bone as primary support and cancellous bone as secondary support, femoral hip implant 10 can achieve greater stability over conventional designs that rely primarily on cancellous bone for support of an implant.

As noted above, collar 18 can be made from a substantially porous material to allow bone ingrowth for long-term stability of the implant. Additionally, distally-extending portion 22 can also be made of porous material to promote stability of the implant by allowing for bone ingrowth along at least a portion of femoral hip implant 10 deeper into the neck 28 of the femur 26. Distal end 16 can be smooth or polished to inhibit bone fixation, allowing the implant to transfer stress to the femoral neck 28 through the circumferential collar 18 while providing end support on the cortical bone of the lateral cortex 24. In addition, by having a portion that inhibits bone ingrowth, the effects of stress shielding can be reduced. Devices which are too stiff or allow for bone attachment throughout their length can cause stress shielding, which can result in bone resorption and loosening of the implant.

Femoral hip implant 10 can achieve both short-term and long-term stability. For example, immediate stability (i.e., 6-8 weeks post-operatively) is achieved by at least the following features: (1) the spherical collar providing proximal support through the cortical bone of the femoral neck; (2) the distal polished tip providing support as it extends through the lateral cortex of the femur; and (3) the use of the central tapered body as a secondary fixation feature, instead of a primary fixation feature. Although the central tapered body exerts some compressive force on the cancellous bone within the neck of the femur, the forces on the cancellous bone are significantly reduced compared to conventional devices.

Long-term stability can be achieved by the same features as noted above for immediate stability, along with additional features provided by bone ingrowth into the implant and stress transfer to the proximal neck area. For example, at least some additional features that enhance long-term stability include (1) the fully porous collar that helps to stress the proximal femoral bone and provide ingrowth; (2) the porous distally-extending portion below the collar that provides for additional bone ingrowth; and (3) the smooth, polished distal tip which passes through the lateral cortex providing end support to the implant and transferring stress to the femoral neck through the collar.

Accordingly, the femoral hip implant described herein allows for greater stability by providing specific bone ingrowth areas at or near the femoral neck 28 to allow for bone fixation, while also providing non-ingrowth areas such that stress is transmitted through the implant to the bone at the bone ingrowth areas, as shown in FIG. 3.

FIGS. 4-6C illustrate an approach for preparing bone for receiving an implant, such as femoral hip implant 10. Conventional femoral implant designs generally require multiple instruments to prepare bone for receiving an implant, which can lead to inaccuracies as each sequential step can accumulate errors and jeopardize the fit of the implant. To reduce these errors, the following method for preparing bone utilizes a biomechanical axial datum a single preparation (i.e., cutting) tool. This approach can provide very precise implant dimensions, allowing for highly repeatable and accurate press-fitting of implants within the bone.

A femoral hip implant (e.g., femoral hip implant 10) is preferably oriented generally parallel to the true neck of the femur. This orientation can be facilitated by using a pin 30 driven through the femoral neck 28 of the femur 26, and then out the lateral cortex 24, as shown in FIG. 4. The pin 30 can be oriented along the axis of the femoral neck, creating an angle 32 with the longitudinal axis of the femur 34. The pin 30 can then be used as a datum to guide a cannulated compound cutter 36 (FIG. 5A), which preferably prepares the femur in one step for the implant. The cutter can be driven by hand or power, and can be composed of three distinct cutting geometries: a spherical proximal cutter 38, a tapered central cutter 40 (tapered towards the distal end), and a cylindrical distal cutter 42, as shown in the enlarged view of cutter 36 in FIG. 5B.

Figure 6B:
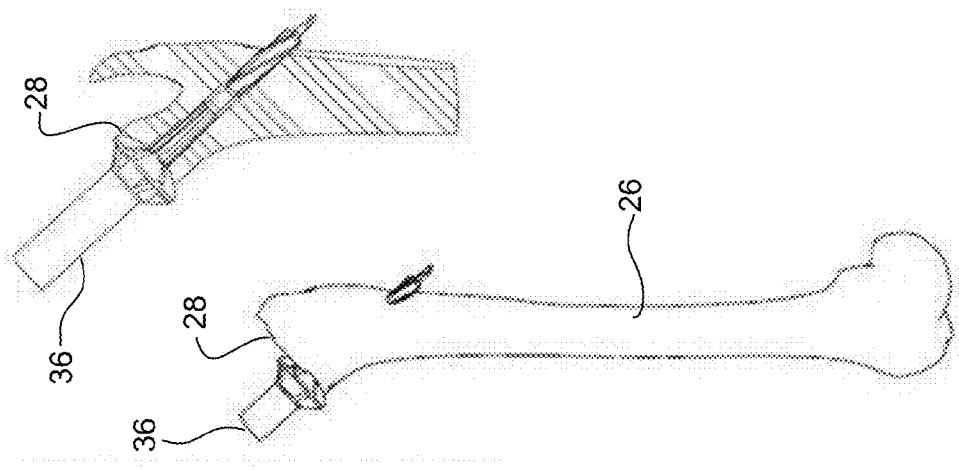
FIG. 6B is a side elevation view showing preparation of a femur with a cannulated compound cutter passed over a pin to enlarge an opening for installation of a femoral implant.
Figure 6A:
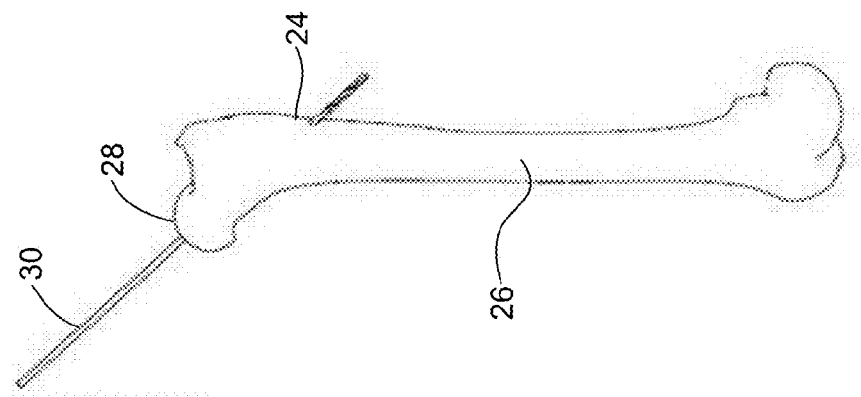
FIG. 6A is a side elevation view showing insertion of a pin into a femur in preparation for insertion of a femoral implant into the femur.

As shown in FIGS. 6A and 6B, after insertion the pin 30 into the femur 26, cutter 36 can be slipped over pin 30 and advanced into the bone through the femoral neck 28 and out the lateral cortex 24, thereby creating an opening or hole. The opening generally approximates the shape of the outer surfaces of the implant; however, the opening is preferably a smaller than the size required by the implant to achieve a tight fit of the implant into the opening. The femoral hip implant 10 can then be press-fitted into the opening, as shown in FIG. 6C. If a greater interference fit is desired, less bone can be removed by cutter 36. For example, in one embodiment, a separate spherical cutter can be used to remove bone at the neck area only, greatly increasing the press fit of the implant.

In some embodiments, the femoral hip implants described herein can be implanted without using any cement to achieve temporary or permanent stability. For example, the above-described embodiments provide implants that can be press-fitted into bone, with the implant configured to allow bone to grow into the implant through one or more porous portions and attach to the implant. Thus, the implants described herein and the methods of use can, in some embodiments, be secured using press-fitting techniques and can be cement-free implants.

Figure 7:
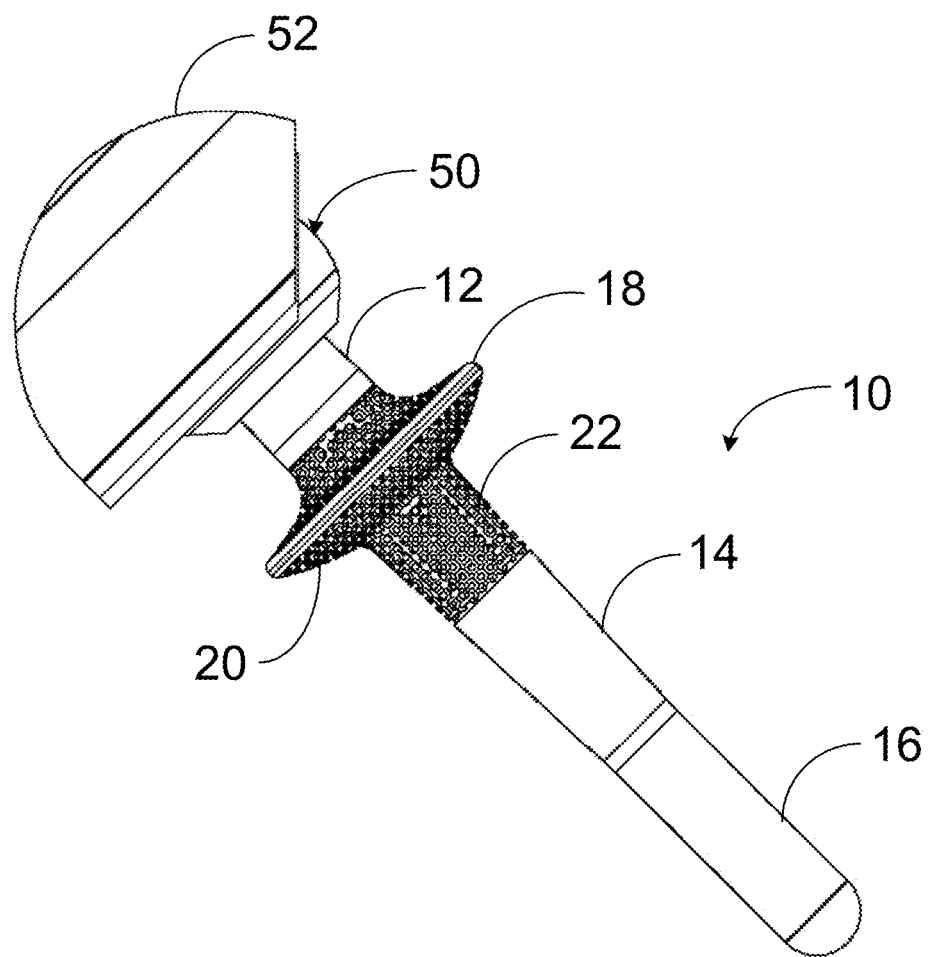
FIG. 7 is a side view of a hip implant system, including a femoral hip implant, a head that can be attached to the femoral hip implant, and an acetabular cup.
Figure 8:
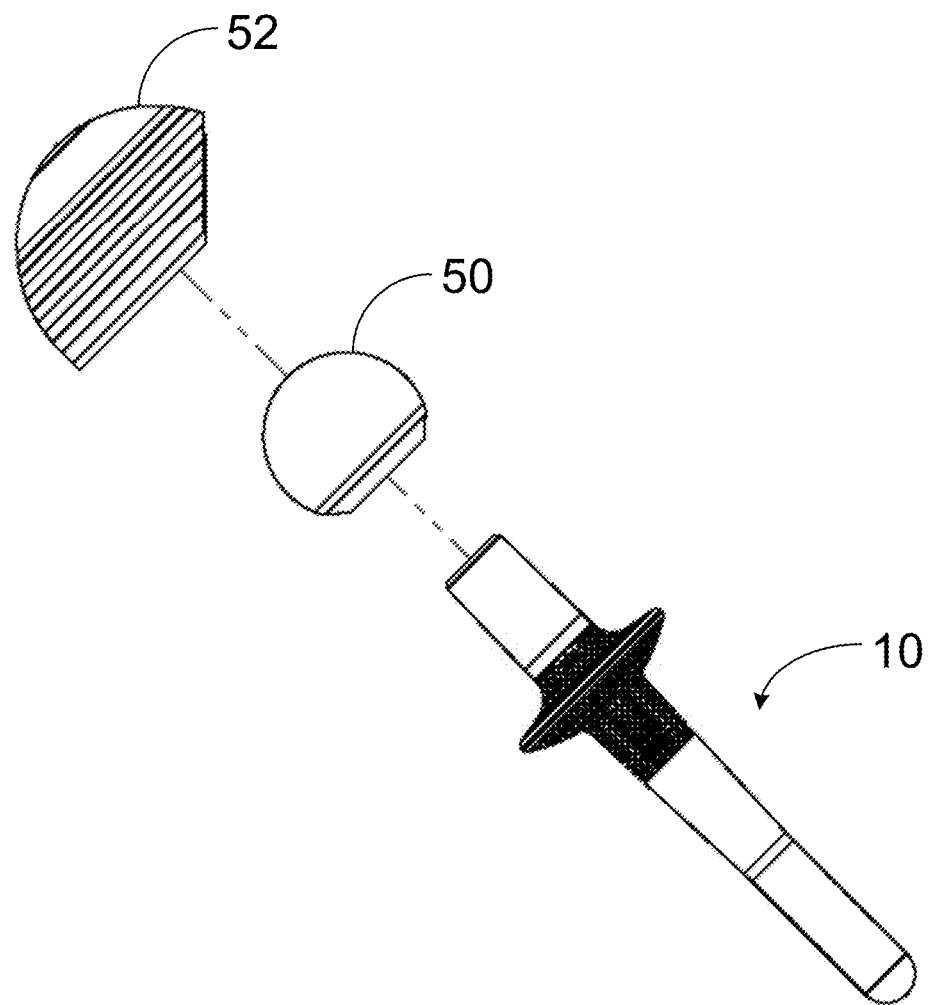
FIG. 8 is an exploded view of the hip implant system shown in FIG. 7.
Figure 9:
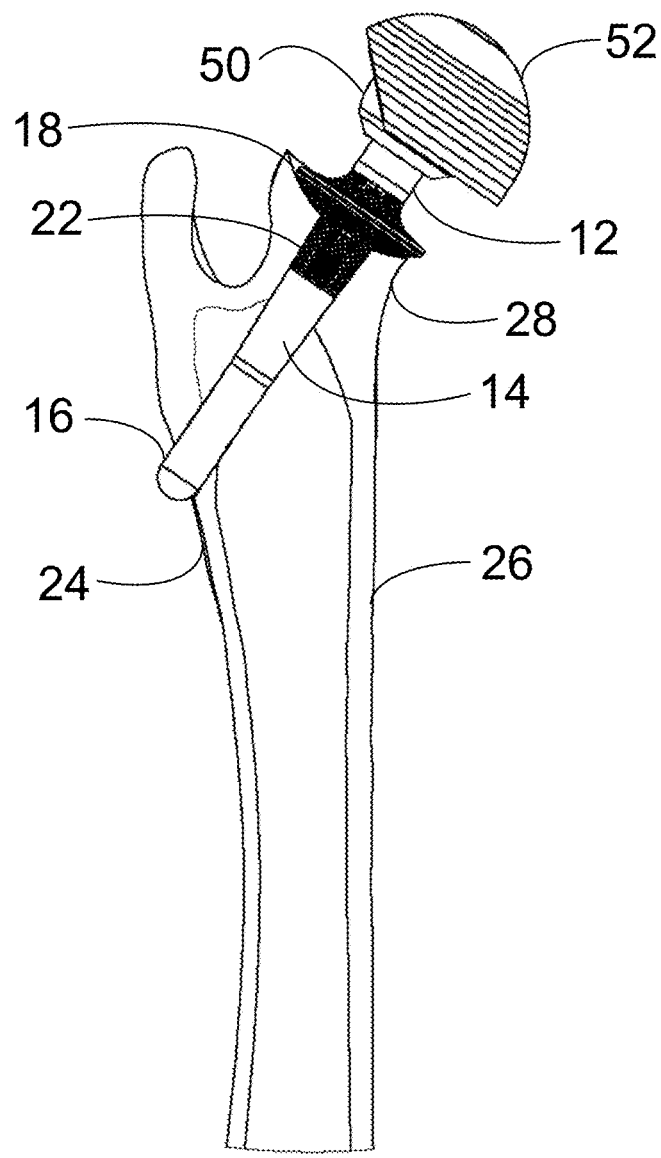
FIG. 9 is a partial cross-sectional view of the hip implant system shown in FIG. 7, illustrated as implanted within a femur.

FIGS. 7-9 illustrate embodiments with a head 50 inserted onto proximal end 12 of femoral hip implant 10. Head 50 is inserted into a cup implant 52, which is inserted into the acetabulum (pelvic bone) of a subject. The femoral hip implant 10 can be used with a variety of head and cup systems in the manner shown in FIGS. 7-9. Cup implants and heads can vary in size to accommodate the particular geometry of the subject. For example, cup implants, in some embodiments, can be provided in sizes that vary from 20-34 mm in size and the heads, in some embodiments, can be provided in sizes from 12 mm to 26 mm. Of course, other sizes are envisioned and can be desirable if the geometry of the subject requires larger or smaller cup implants and heads.

Figure 10:
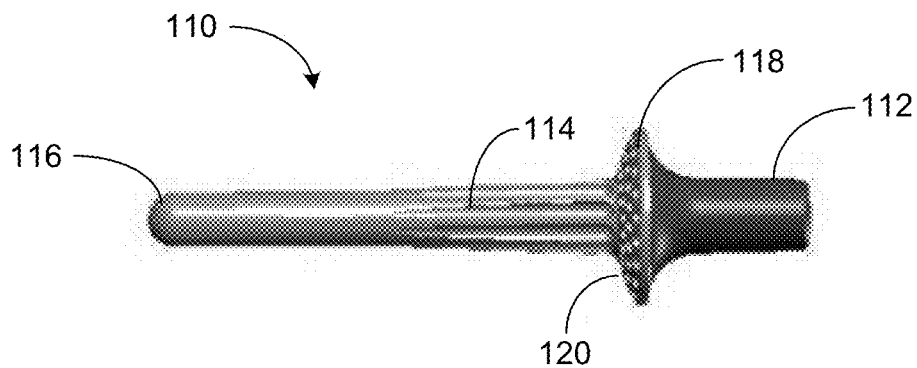
FIG. 10 is a side view of a hip implant system.
Figure 11:
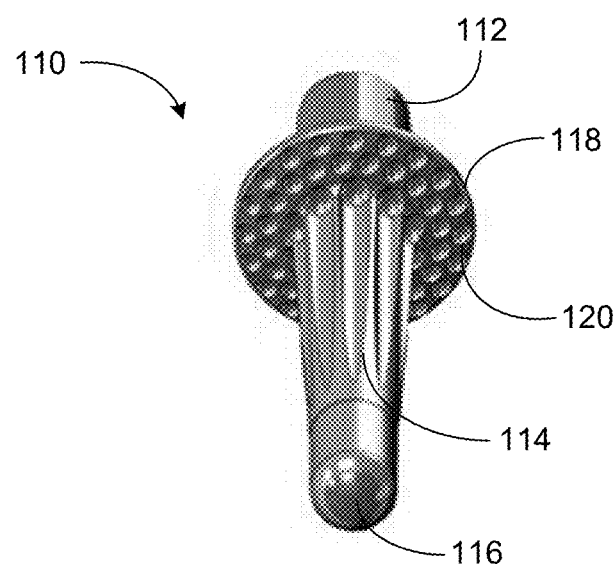
FIG. 11 is a front perspective view of the hip implant system shown in FIG. 10.
Figure 12:
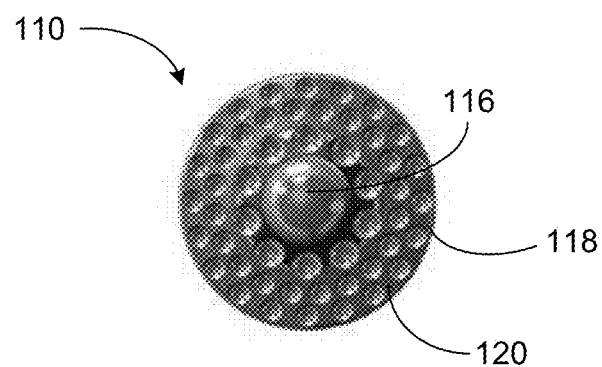
FIG. 12 is a bottom view of the hip implant system shown in FIG. 10.

FIGS. 10-12 illustrate another embodiment of a femoral hip implant 110. Femoral hip implant 110 is similar to femoral hip implant 10; however, femoral hip implant 110 is configured to allow bone ongrowth—instead of ingrowth—on one or more areas of the implant. Femoral hip implant 110 comprises a proximal end 112, a centrally tapered body 114 with a distal end 116, and a circumferential collar 118 between proximal end 112 and centrally tapered body 114. Collar 118 can comprise a substantially spherical distal surface 120. As discussed above, the spherical surface of the collar can provide improved stress distribution.

Spherical distal surface 120 can be textured to encourage bone ongrowth. FIGS. 10-12 illustrate an embodiment in which the surface 120 is macro-textured. In some embodiments, this texture can comprise a plurality of indentations that are sized to allow growth of bone into the indentations or dimples to restrict movement of implant 110 after implantation. In some embodiments, centrally tapered body 114 can also have a portion that allows bone on growth. Thus, for example, centrally tapered body 114 can also have a plurality indentations, such as the grooves indicated in FIG. 11, that allow for bone ongrowth. Proximal and distal ends 112, 116 can comprise solid surfaces, such as a smooth polished surface. These surfaces preferably restrict bone ingrowth or ongrowth.

To further promote bone growth (i.e., ongrowth or ingrowth) where desired, portions of the implants described herein can be coated with hydroxyapatite (HA) or other coatings that can increase or facilitate bone growth on the implant.

The implants described herein can be formed of various biocompatible materials. In some embodiments, the implants can be formed of titanium alloys, such as ASTM F-136 (Ti6A14V ELI Titanium Alloy). In other embodiments, the implants can be formed using other biocompatible materials, such as cobalt chromium, stainless steel, and various composite materials or plastics.

The porous portions of the implant described herein can be formed in various ways. For example, in one embodiment, the implant can be formed using additive manufacturing techniques. Additive manufacturing techniques can include electron beam melting (EEM) whereby the implant can be produced by building the implant layer-by-layer from metal powder (e.g., a titanium alloy powder) using a powerful electron beam. Another additive manufacturing technique that can be used to produce the implants described herein is laser-sintering, such as that provided by EOS GmbH in Munich, Germany. These techniques can be used to produce an implant with the desired porous portions (for bone ingrowth) or indentations (for bone ongrowth), as well as the other portions of the implant which are intended to restrict bone in-growth and on-growth.

The implants described herein can also be produced using other more conventional techniques, including, for example, conventional machining processes. In some embodiments, for example, the porous portions of the implant can be created by layering a plurality of beads (or other elements) on top of one another to create a plurality of layers of beads. The beads can be fused to one another and to the implant body to form gaps into which bone can grow.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A bone implant apparatus, comprising:
    a proximal end portion;
    a central tapered body defined by a proximal tapered portion and a distal end tapered portion, the proximal tapered portion and distal end tapered portion forming one contiguous tapered shape; and
    a circumferential collar between the proximal end portion and the distal end tapered portion of the central tapered body, the circumferential collar comprising a proximal surface and a substantially spherical distal surface;
    wherein the proximal tapered portion of the central tapered body extends from the collar toward the distal end tapered portion,
    wherein the proximal surface, substantially spherical distal surface, and proximal tapered portion of the central tapered body comprise a porous material capable of allowing bone ingrowth into the proximal surface, substantially spherical distal surface, and proximal tapered portion of the central tapered body, such that the porous material is continuous from the substantially spherical distal surface to the proximal tapered portion of the central tapered body,
    wherein the proximal end portion is integral with the distal end tapered portion forming a main shaft, and the collar extends outward from the main shaft between the proximal end portion and the distal end tapered portion, and
    wherein the proximal tapered portion is a porous body disposed circumferentially around the main shaft distal to the circumferential collar.

2. The apparatus of claim 1, wherein the distal end tapered portion is substantially smooth and formed of a material that restricts bone ingrowth.

3. The apparatus of claim 1, wherein the proximal end portion is tapered, the proximal end portion being at its widest in the vicinity of the collar and at its narrowest furthest from the collar.

4. The apparatus of claim 1, wherein the bone implant apparatus is configured to be implanted without using any cement or other bonding agents to bond the implant to a femur.

5. The apparatus of claim 1, wherein the bone implant apparatus is sized to be sufficiently long so that at least a portion of the distal end tapered portion extends through a lateral cortex of a femur of a subject when implanted in the subject's femur.

6. The apparatus of claim 1, wherein the collar is a separate structure that is secured to the main shaft.

* * * * *